US008692016B2

(12) United States Patent
Sanders et al.

(10) Patent No.: US 8,692,016 B2
(45) Date of Patent: Apr. 8, 2014

(54) GAS-PHASE PHOSGENATION PROCESS

(75) Inventors: Josef Sanders, Leverkuse (DE); Hanno Brummer, Dusseldorf (DE); Jorg Laue, Dormagen (DE); Bernd Sojka, Cologne (DE); Marcus Eichmann, Dusseldorf (DE); Verena Haverkamp, Bergisch Galdbach (DE)

(73) Assignee: Bayer MaterialScience AG, Leverkusen (DE)

( * ) Notice: Subject to any disclaimer, the term of this patent is extended or adjusted under 35 U.S.C. 154(b) by 856 days.

(21) Appl. No.: 12/855,073

(22) Filed: Aug. 12, 2010

(65) Prior Publication Data

US 2010/0312009 A1 Dec. 9, 2010

Related U.S. Application Data

(63) Continuation of application No. 11/494,419, filed on Jul. 27, 2006.

(30) Foreign Application Priority Data

Aug. 2, 2005 (DE) .......................... 10 2005 036 870

(51) Int. Cl.
*C07C 263/00* (2006.01)
(52) U.S. Cl.
USPC ........... 560/347; 165/164; 165/165; 165/166; 165/167; 159/47.1; 422/203

(58) Field of Classification Search
None
See application file for complete search history.

(56) References Cited

U.S. PATENT DOCUMENTS

| 4,847,408 A * | 7/1989 | Frosch et al. ................. 560/347 |
|---|---|---|
| 6,225,497 B1 | 5/2001 | Becker et al. |
| 6,706,913 B2 | 3/2004 | Leimkuhler et al. |
| 6,800,781 B2 | 10/2004 | Herold et al. |
| 6,930,199 B2 | 8/2005 | Meyn et al. |
| 7,019,164 B2 | 3/2006 | Friedrich et al. |
| 2003/0013909 A1 | 1/2003 | Leimkuhler et al. |
| 2003/0069441 A1 | 4/2003 | Leimkuhler et al. |
| 2003/0103879 A1* | 6/2003 | Jahn et al. ..................... 422/211 |
| 2003/0114705 A1 | 6/2003 | Friedrich et al. |
| 2004/0068137 A1 | 4/2004 | Herold et al. |
| 2005/0022940 A1* | 2/2005 | Kupper et al. ............... 159/47.1 |
| 2005/0113601 A1 | 5/2005 | Herold et al. |
| 2005/0137417 A1 | 6/2005 | Meyn et al. |

FOREIGN PATENT DOCUMENTS

| EP | 1486749 A2 * | 12/2004 |
| WO | 0056160 A1 | 9/2000 |
| WO | 0165194 A1 | 9/2001 |

* cited by examiner

*Primary Examiner* — Sudhakar Katakam
(74) *Attorney, Agent, or Firm* — Robert S. Klemz

(57) ABSTRACT

The present invention relates to a process for the phosgenation of amines in the gas phase, in which a specific type of heat exchanger is used for vaporizing the amines.

14 Claims, No Drawings

GAS-PHASE PHOSGENATION PROCESS

This is a Continuation application of U.S. Ser. No. 11/494,419 filed Jul. 27, 2006.

BACKGROUND OF THE INVENTION

The present invention relates to a process for the phosgenation of amines in the gas phase, in which a specific type of heat exchanger is used for vaporizing the amines.

EP-A 0 289 840 describes a process for preparing (cyclo) aliphatic diisocyanates by phosgenation of the corresponding gaseous (cyclo)aliphatic diamines at from 200° C. to 600° C. Phosgene is introduced in a stoichiometric excess. The superheated streams of gaseous (cyclo)aliphatic diamine or (cyclo) aliphatic diamine/inert gas mixture and of phosgene are introduced continuously into a cylindrical reaction space and mixed with one another and reacted there. The exothermic phosgenation reaction is carried out while maintaining turbulent flow.

EP-A 928 785; EP-A 1 319 655; EP-A 1 555 258; EP-A 1 275 639; EP-A 1 275 640; EP-A 1 403 248; and EP-A 1 526 129 each describes a specific embodiment of this technology, but these disclosures relate to the reactor itself and the reaction conditions without going into details about the vaporizer technology used for pre-treatment of the starting materials.

Shell-and-tube heat exchangers, plate heat exchangers or falling film evaporators, preferably with a pumped circuit, are customarily used for heating and vaporizing the starting materials used, i.e., amines and phosgene. Heater coils matrices operated electrically or by means of heat transfer fluids are used for heating the gaseous amines. However, these apparatuses have the disadvantage that the relatively high film thicknesses which occur adversely affect mass transfer and heat transfer, so that an increased residence time is required. As a result, decomposition with elimination of ammonia occurs, particularly in the vaporization and superheating of aliphatic amines. This not only reduces the yield but also causes the formation of deposits of ammonium chloride in pipes and the reactor in the subsequent phosgenation reaction. The plants therefore have to be cleaned relatively frequently, resulting in corresponding losses of production.

Micro heat exchangers or micro vaporizers have been described in WO 2005/016512 but only in the context of removal of compounds from liquid mixtures by distillation. However, in the field of gas-phase phosgenation of amines to form isocyanates, these apparatuses have not been described in any respect nor have their possible advantages been mentioned.

SUMMARY OF THE INVENTION

It was therefore an object of the present invention to provide a process for the phosgenation of amines in the gas phase, in which the above-mentioned disadvantages of conventional heat exchangers or vaporizers are avoided.

This object has now been achieved by the use of milli or micro heat exchangers for the liquid heating, vaporization and gas superheating of the amines.

DETAILED DESCRIPTION OF THE INVENTION

The present invention provides a process for preparing isocyanates by phosgenation of amines in the gas phase, in which one or more heat exchangers having (1) a heat transfer area per unit volume for the amine side of at least 1,000 $m^2/m^3$ and (2) channels having a hydraulic diameter of from 5 to 10,000 µm for the flow of the amines are used for liquid heating, vaporization and/or gas superheating of the amines.

Depending on the diameter of the channels, such heat exchangers or vaporizers are also known as milli heat exchangers or vaporizers (diameters of the flow channels of ≥1,000 µm) or micro heat exchangers or vaporizers (diameters of the flow channels of <1,000 µm).

These vaporizers or heat exchangers used in accordance with the present invention have a smaller volume than conventional heat exchangers for the same performance. As a result, the residence time and thus also the thermal stress to which the amines are subjected is considerably reduced. The vaporization and thus the residence time is typically from 10 to 100 times faster or shorter than in the case of conventional systems.

As amines, it is in principle possible to use any compound having primary amino groups which is known to those skilled in the art for the phosgenation. However, compounds having at least 2, preferably 2 or 3, $NH_2$ groups which may be aliphatically, cycloaliphatically or aromatically bound are preferred.

Examples of suitable amines are the pure isomers or the isomer mixtures of diaminobenzene, diaminotoluene, diaminodimethylbenzene, diaminonaphthalene and diaminodiphenylmethane. 2,4-/2,6-toluenediamine mixtures having isomer ratios of 80/20 and 65/35 and the pure 2,4-toluenediamine isomer are preferred.

Suitable aliphatic or cycloaliphatic amines include: 1,4-diaminobutane; 1,6-diaminohexane (HDA); 1,11-diaminoundecane; 1-amino-3,5,5-trimethyl-5-aminomethylcyclohexane (IPDA); 4,4'-diaminodicyclohexylmethane; 2,2-bis(4-aminocyclohexyl)propane; and 1,8-diamino-4-(aminomethyl)octane (triaminononane).

However, particular preference is given to diamines and/or triamines of the above-mentioned type which have exclusively aliphatically or cycloaliphatically bound amino groups, e.g. isophoronediamine (IPDA), hexamethylenediamine (HDA), his(p-aminocyclohexyl)methane (PACM 20) and 1,8-diamino-4-(aminomethyl)-octane (triaminononane).

The basic principle of gas-phase phosgenation is comprehensively described in the above-mentioned EP applications.

In such a phosgenation process, the liquid amines to be phosgenated and the phosgene are first vaporized separately, if appropriate, diluted with an inert gas or with the vapor of an inert solvent, if appropriate, gas-superheated and then reacted continuously in a usually cylindrical reaction space having no moving parts in which turbulent flow prevails and which is typically heated to from 200 to 600° C. The gas mixture which continuously leaves the reaction space is then cooled, preferably by means of an inert liquid solvent which is maintained at a temperature above the decomposition temperature of the carbamoyl chloride corresponding to the amine, to give a solution of the corresponding isocyanate in this solvent and the isocyanate present in solution in the inert solvent is separated off, for example, by distillation.

Milli or micro heat exchangers suitable for the purposes of the present invention are, for example, stacked channel micro heat exchangers and stacked channel milli heat exchangers. If these are used for vaporization, they are correspondingly referred to as stacked channel micro vaporizers and stacked channel milli vaporizers. These are typically made up in a layered fashion of thin metal plates which each have a multiplicity of parallel channels in which flow occurs. The plates are, for example, arranged crosswise so that the channels of one plate are perpendicular to the channels of the plate located below and/or above it. Accordingly, the heat transfer medium and the reaction mixture are conveyed through the heat exchanger or vaporizer according to the cross-flow principle in such arrangements: the heating medium and the reaction mixture flow through alternate layers.

The plates have, for example, a thickness of from 100 to 1,000 µm. The individual channels each typically have a length of from 0.5 to 400 cm, preferably from 1 to 150 cm.

Such stacked channel heat exchangers are suitable both as milli heat exchangers and as micro heat exchangers for the process of the invention.

Regardless of the geometry of the channels of the micro or milli heat exchangers (or vaporizers), the hydraulic diameter (D) is the characterizing parameter for the purposes of the present invention. The hydraulic diameter (D) is equal to four times the cross-sectional area of the channel (A) divided by the circumference (C) of the channel cross section :

$$D=4\, A/C$$

Such stacked channel micro heat exchangers are marketed, for example, by the Forschungszentrum Karlsruhe and are described in K. Schubert, J. Brandner, M. Fichtner, G. Linder, U. Schygulla, A. Wenka, "Microstructure devices for applications in thermal and chemical process engineering, Heat and Transport Phenomena in Microsystems". Proc. Of the Internat. Conf., Banff. Oct. 15-20, 2000.

Instead of the above-described stacked channel heat exchangers or vaporizers. specific tube heat exchangers or vaporizers which meet the above-defined criteria for the heat transfer area per unit volume and the hydraulic diameter of the channels for the flow of the amines can also be used in the process of the invention. They are therefore referred to as channel tube heat exchangers.

These channel tube heat exchangers have one or more parallel tubes for the flow of the amines arranged in an enclosed surrounding space instead of stacked channels. The heat transfer medium flows through the surrounding space. Such specific tube heat exchangers corresponding to the above-mentioned criteria can have one or more channel tubes arranged in a parallel fashion. The surrounding space of such tube heat exchangers is preferably provided with deflection plates which improve the flow conditions and thus the heat transfer. The heat transfer medium can flow through the surrounding space either in co-current or in counter-current.

The channel tubes used in such specific tube heat exchangers each usually have a length of from 10 cm to 400 cm. preferably from 30 to 150 cm. The wall thickness of the tubes is usually from 0.5 to 6 mm.

Such tube heat exchangers which meet the criteria according to the invention for the heat transfer area per unit volume and the hydraulic diameter of the channels for the flow of the amines are in principle suitable both as milli heat exchangers and as micro heat exchangers for the process of the invention. However, preferred tube heat exchanges are milli channel tube heat exchangers.

If micro heat exchangers or vaporizers of the above-described type, for example, in the form of stacked channel micro heat exchangers or micro channel tube heat exchangers, are used, the hydraulic diameter of the channels for conveying the amine stream is preferably at least 5 µm but less than 1,000 µm, more preferably from 30 to 500 µm.

If milli heat exchangers or vaporizers of the above-described type, for example, in the form of stacked channel milli heat exchangers or milli channel tube heat exchangers, are used, the hydraulic diameter of the channels for conveying the amine steam is preferably from 1,000 to 10,000 µm, more preferably from 2,000 to 5,000 µm.

At the same time, the heat exchange area per unit volume of the amine channels is preferably from $1\times10^3$ to $1\times10^5$ m$^2$/m$^3$ in micro heat exchangers of the above-described type, more preferably from $2\times10^3$ to $1\times10^5$ m$^2$/m$^3$ and in milli heat exchangers of the above-described type preferably from 1 to $2\times10^3$ m$^2$/m$^3$.

In stacked channel micro heat exchangers and stacked channel milli heat exchangers, the channels for conveying the heating medium preferably have a hydraulic diameter of from 5 to 10,000 µm, more preferably from 5 to 1,000 µm, most preferably from 30 to 500 µm.

The channels of the micro or milli heat exchangers for conveying the amines and the heating medium can have any geometric shape. The cross section of the channels can be, for example, round, semicircular, angular, rectangular or triangular. The channels are preferably rectangular or triangular and in the case of milli channel tube heat exchangers can also be oval.

The flow channels can in principle also contain internals. This increases heat transfer compared to systems in which no such internals are present. The internals can also be fixed to the channels. In this case, the internals additionally act as heat transfer fins by means of which heat transfer is additionally added.

Such internals can, for example, be layer structures. Such structures are generally made up of at least three layers, with each structured layer in the installed state having a multiplicity of openings which are arranged in at least one longitudinal row and the openings of a middle layer intersecting with at least three openings of an adjacent layer so that the sequence of the intersecting openings forms a flow channel in the longitudinal direction or transverse direction of the layers. Such structures can be formed by use of metal sheets having a sequence of obliquely arranged openings, as described in EP-A 1 284 159. Instead of metal sheets with openings, it is also possible to use comb profile layers as described in EP-A1 486 749. Here, it can be particularly useful to employ symmetrical, two-sided comb profiles which divide the channel interior into two separate parallel channel zones.

The openings of the metal sheet structures or the comb teeth of the comb structures are arranged at an angle of from 5 to 85°, preferably from 30 to 60°, to the main flow direction. The number of openings or comb teeth in a structured layer to form a series of openings is preferably at least 50, more preferably at least 200, most preferably at least 500.

A micro or milli heat exchanger channel filled with structured layers is particularly advantageous in terms of back mixing and the temperature profile when the ratio of channel length (L) to the hydraulic diameter of the channel (D) (the L/D ratio) is greater than 10, preferably greater than 100 and more preferably greater than 500.

Micro and milli channels having a rectangular or oval cross section are particularly well-suited to the use of layer structures.

Preference is given to using internals in milli vaporizers or heat exchangers, i.e. apparatuses of this type for heating, vaporization and/or superheating, which have channels for the flow of the amines with a diameter of ≥1,000 µm.

The layer structure internals for such milli heat exchangers typically have a thickness of from 0.1 to 3 mm, preferably from 0.5 to 1.5 mm. The channels which are built into the structures typically have a height of from 1 to 10 mm, preferably from 2 to 5 mm, and a width of from 5 to 50 mm, preferably from 10 to 30 mm.

In stacked channel micro heat exchangers and stacked channel milli heat exchangers, not only the channels for the flow of the amines but also channels through which the heating medium is conveyed can be configured in this way. This can be useful in order to improve heat transfer to the heat transfer side, too.

The micro or milli heat exchangers or micro or milli vaporizers can be made of any metallic material, e.g. steel, stainless steel, titanium, Hastelloy, Inconel or other metallic alloys.

As heating medium, it is possible to use the customary heating media such as steam, pressurized water or heat transfer fluids.

The temperature at which the heater heat exchanger or vaporizer heat exchanger used according to the invention is operated depends on the boiling point of the amine to be vaporized. The aim is for the temperature after passage through the heater heat exchanger to be just below the boiling point of the amine and for all the previously liquid amine to be brought into the gas phase after passage through the vaporizer and, if appropriate, for the gaseous amine to be superheated in the same heat exchanger or a further heat exchanger. Circulating flows through the apparatuses are deliberately dispensed with, so that the amine passes through the apparatuses only once. This has the advantage that the volume of pump reservoirs which are otherwise necessary can also be dispensed with and the residence time at high temperatures is reduced further. The precise pressure and temperature conditions can easily be determined by a person skilled in the art by means of routine experiments.

In the vaporization of phosgene before entry into the reactor, a temperature of the phosgene stream of from 250 to 500° C., more preferably from 280 to 330° C., is preferably set, with the (absolute) pressure typically being from 500 to 2,400 mbar, preferably from 700 to 1,500 mbar.

In the process of the present invention, the amines are preferably brought to a temperature of the amine stream of from 200 to 500° C., more preferably from 280 to 350° C., before entry into the reactor, with the (absolute) pressure typically being from 500 to 2,500 mbar, preferably from 800 to 1,600 mbar.

In the process of the invention, the mean residence time of the amines in the heater is preferably from 0.001 to 60 s, more preferably from 0.01 to 10 s.

In the process of the invention, the mean residence time of the amines in the vaporizer is preferably from 0.001 to 60 s, more preferably from 0.01 to 10 s.

In the process of the invention, the mean residence time of the amines in the gas superheater is preferably from 0.0001 to 10 s, more preferably from 0.0005 to 1 s.

In principle, the respective heating, vaporization and, if appropriate, superheating using the micro and milli heat exchangers or vaporizers to be used according to the invention is carried out in one or more stages using a plurality of such milli and micro structural components connected in parallel and/or in series. In the case of multistage processes, the vaporization can also be carried out at different pressure and temperature levels.

An advantage of the process of the invention is that, due to the short residence times and therefore low integral temperature stresses in the milli and micro structural components, decomposition of temperature-sensitive aliphatic amines is reduced compared to conventional vaporizers or is avoided completely. In addition, the surface-to-volume ratio is increased in the vaporization due to the geometrically dictated formation of small bubbles, so that very efficient vaporization is possible. These advantages result in a higher yield and higher product quality. Furthermore, due to the reduced elimination of ammonia in the subsequent phosgenation reaction, a small amount of ammonium chloride is formed, so the plant becomes fouled less quickly and the run times between stoppages for cleaning can therefore be increased.

After leaving their respective vaporizers, the feed streams can also be passed over internals which enable better mixing of the reactants in the gas space to be achieved. Similar measures can also be taken in the reactor itself in order to improve the mixing of amine and phosgene and thus ensure substantially trouble-free continuous operation. Examples of such measures are the installation of swirl-inducing internals in the feed lines or a tapering diameter of the reactor tube downstream of the confluence of the amine stream and the phosgene stream. Further suitable measures may be found in the published patents and applications discussed herein.

The feed streams can also be diluted with inert diluents before being fed into the reaction space. A preferred inert gas for dilution is nitrogen. Suitable inert solvents whose vapors can likewise be used for diluting diamine are, for example, chlorobenzene, o-dichlorobenzene, xylene, chloronaphthalene, decahydronaphthalene and mixtures thereof.

The amount of any inert gas or solvent vapor used as diluent is not critical, but can be utilized to reduce the vaporization temperature of the amine.

In the phosgenation of diamines, the molar excess of phosgene per amino group is usually from 30 to 300%, preferably from 60 to 170%.

Suitable cylindrical reaction spaces are, for example, tube reactors without internals and without moving parts in the interior of the reactor. The tube reactors are generally made of steel, glass, alloy steel or enamelled steel and have a length which is sufficient to allow complete reaction of the amine with the phosgene under the process conditions. The gas streams are generally fed into the tube reactor at one end of the reactor, for example, through nozzles installed at one end of the tube reactor or through a combination of nozzle and an annular gap between nozzle and a mixing tube. The mixing tube is likewise maintained at a temperature within the range from 200 to 600° C., preferably from 300 to 500° C., with this temperature being maintained, if necessary, by heating of the reaction tube.

During operation of the process of the invention, the pressure in the feed lines to the reaction space is generally from 200 to 3,000 mbar and that at the output from the reaction space is generally from 150 to 2,000 mbar, with care being taken to ensure a flow velocity within the reaction space of at least 3 m/s, preferably at least 6 m/s and more preferably from 10 to 120 m/s, by maintaining an appropriate differential pressure. Under these conditions, turbulent flow generally prevails within the reaction space.

After the phosgenation reaction has occurred in the reaction space, the gaseous mixture which continuously leaves the reaction space is freed of the isocyanate formed. This can be effected, for example, by means of an inert solvent whose temperature is selected so that it is (1) above the decomposition temperature of the carbamoyl chloride corresponding to the isocyanate and (2) below the condensation temperature of the isocyanate and, preferably, also that of any solvent used in vapor form as diluent, so that isocyanate and auxiliary solvent condense or dissolve in the solvent while excess phosgene, hydrogen chloride and any inert gas used as diluent pass through the condensation stage or the solvent in gaseous form. Solvents of the types which have been mentioned by way of example above, in particular technical-grade dichlorobenzene, which are maintained at a temperature of from 120 to 200° C., preferably from 120 to 170° C., are particularly well-suited for the selective recovery of the isocyanate from the mixture leaving the reaction space in gaseous form. Conceivable methods of selectively condensing the isocyanate formed from the gas mixture leaving the reactor using such solvents are, for example, passing the gas mixture through the respective solvent or spraying the solvent (solvent mist) into the gas stream.

The gas mixture passing through the condensation stage for recovering the isocyanate is subsequently freed of excess phosgene in known manner. This can be effected by means of a cold trap, absorption in an inert solvent (e.g., chlorobenzene or dichlorobenzene) maintained at a temperature of from −10° C. to 8° C. or by adsorption and hydrolysis on activated carbon. The hydrogen chloride gas which passes through the phosgene recovery stage can be recycled in a manner known to those skilled in the art for recovery of the chlorine required for the phosgene synthesis.

Isolation of the isocyanates in pure form is best achieved by work-up of the solution of the isocyanate in the solvent used for the isocyanate condensation by distillation.

EXAMPLES

The suitability of the milli and micro heat exchangers for the vaporization and superheating of amines under relatively mild conditions was demonstrated in an experimental plant. Amines used were 1,6-diaminohexane (HDA), 1-amino-3,5, 5-trimethyl-5-aminomethylcyclohexane (IPDA) and 4,4'-diaminodicyclohexylmethane (PACM 20).

A plurality of milli heat exchangers each having rectangular flow channels were connected in series and were in each case used for heating, vaporization and superheating. The flow channels had an internal height of 3.1 mm, an internal width of 18 mm and were filled with a layer structure. This filling was made up of three layers each of which had a height of 1 mm. The total length of the channels per vaporizer was 300 mm. The heat transfer area (arithmetic mean of internal and external wall area) per channel was 156 cm$^2$ and the free internal volume was 12.8 cm$^3$.

For heating, three such milli heat exchangers were connected in series to form a countercurrent heat exchanger (MHE 1-MHE 3).

For vaporization, two of these milli heat exchangers were connected in series to form a countercurrent heat exchanger (MHE 4-MHE 5).

All milli heat-exchanger apparatuses had an interior shell diameter of about 40 mm and were provided with a plurality of deflection plates in the volume within the shell through which heat transfer medium flowed.

In the heating procedure, the amines were heated from 60° C. to the boiling point in the first heat exchanger series (MHE 1-MHE 3) and then vaporized and superheated in the second heat exchanger series (MHE 4-MHE 5). The amine was condensed in the downstream condenser, fed into the receiver and subsequently pumped around the circuit again.

To monitor chemical changes in the amines, samples were analyzed by gas chromatography and ammonia analysis at regular intervals.

A pressure buildup occurring over time in conventional heat exchangers as a result of deposits was observed for none of the amines used during the time of the experiment.

Example 1

HDA was heated to 217° C. at a pressure of 2.3 bara (pressure in bar absolute) in the MHE 1-MHE 3 heated to 224° C. and then vaporized and superheated to 305° C. at a pressure of 1.0 bara in the MHE 4-MHE 5 heated to 307° C. At a pump circulation rate of 20 kg/h, the mean residence time in MHE 1-MHE 3 was 4.7 s and in MHE 4-MHE 5 was 9.4 s, assuming complete liquid flow as far as the outlet. The real residence time was significantly below this value because of vaporization. After 80 statistical passes, the concentration of secondary components increased from 170 ppm to 270 ppm.

Heat transfer coefficients determined were: from 1,200 to 1,700 W/(m2K) for heating to the boiling point at pump circulation rates of from 20 to 40 kg/h, 1,800 W/(m$^2$K) for vaporization at a pump circulation rate of 40 kg/h and from 100 to 500 W/(m$^2$K) for superheating at pump circulation rates of from 5 to 20 kg/h.

Example 2

IPDA was heated to 260° C. at a pressure of 1.6 bara in the MHE 1-MHE 3 heated to 277° C. and then vaporized and superheated to 302° C. at a pressure of 1.0 bara in the MHE 4-MHE 5 heated to 305° C. At a pump circulation rate of 20 kg/h, the mean residence time in MHE 1-MHE 3 was 5.2 s and in MHE 4-MHE 5 was 10.5 s, assuming complete liquid flow as far as the outlet. The real residence time was significantly below this value because of vaporization. After 80 statistical passes, the concentration of secondary components increased from 1,300 ppm to 2,200 ppm.

Heat transfer coefficients determined were: from 500 to 1,650 W/(m$^2$K) for heating to the boiling point at pump circulation rates of from 10 to 110 kg/h, 1,800 W/(m$^2$K) for vaporization at a pump circulation rate of 20 kg/h and from 200 to 300 W/(m$^2$K) for superheating at pump circulation rates of from 10 to 15 kg/h.

Example 3

PACM 20 was heated to 327° C. at a pressure of 1.2 bara in the MHE 1-MHE 3 heated to 338° C. and then vaporized and superheated to 335° C. at a pressure of 1.0 bara in the MHE 4-MHE 5 heated to 352° C. At a pump circulation rate of 15 kg/h, the mean residence time in MHE 1-MHE 3 was 7 s and in MHE 4-MHE 5 was 14 s, assuming complete liquid flow as far as the outlet. The real residence time was significantly below this value because of vaporization. After 60 statistical passes, the concentration of secondary components increased from 3,900 ppm to 4,400 ppm.

Heat transfer coefficients determined were: from 350 to 1.850 W/(m$^2$K) for heating to the boiling point at pump circulation rates of from 10 to 100 kg/h, 900 W/(m$^2$K) for vaporization at a pump circulation rate of 15 kg/h and 250 W/(m$^2$K) for superheating at pump circulation rates of 15 kg/h.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing an isocyanate comprising phosgenating an amine
in the gas phase in which at least one heat exchanger having
   a. a heat transfer area per unit volume for the amine side of at least 1,000 m$^2$/m$^3$ and
   b. channels with a hydraulic diameter of from 1,000 to 10,000 μm for the flow of the amine
is used for liquid heating, vaporization and/or gas superheating of the amine.

2. The process of claim 1 in which the amine is flowed through a heat exchanger having an individual channel length of from 0.5 to 400 cm.

3. The process of claim 1 in which the amine is flowed through a heat exchanger comprising at least one stacked channel micro heat exchanger or milli channel tube heat exchanger type having channels with hydraulic diameters of from 2,000 to 5,000 μm and an individual channel length of from 10 to 400 cm.

4. The process of claim 1 in which a. is from $1 \times 10^3$ to $1 \times 10^5$ m$^2$/m$^3$.

5. The process of claim 1 in which the channels of the heat exchanger through which amine is flowed contain internals.

6. The process of claim 5 in which channels or space of the heat exchanger for conveying a heating medium contain internals.

7. The process of claim 1 in which channels or space of the heat exchanger for conveying a heating medium contain internals.

8. The process of claim 1 in which the amine's mean residence time in the heat exchanger for heating and/or vaporizing is in each case from 0.01 to 10 s.

9. The process of claim 8 in which the amine has a mean residence time in the heat exchanger for gas superheating of from 0.0005 to 1 s.

10. The process of claim 1 in which the amine's mean residence time in the heat exchanger for gas superheating is from 0.0005 to 1 s.

11. The process of claim 1 in which the amine is heated to a temperature of from 280 to 350° C. at an (absolute) pressure of from 800 to 1.600 mbar before entering the reactor.

12. Process according to any of claims 1 to 7, characterized in that the phosgene is heated to a temperature of the phosgene stream of from 280 to 330° C. at an (absolute) pressure of from 700 to 1.500 mbar before entering the heat exchanger for phosgenation.

13. The process of claim 1 in which phosgene is used in a molar excess per amino group to be phosgenated of from 60 to 170%.

14. The process of claim 1 in which isophoronediamine (IPDA), hexamethylenediamine (HDA), bis(p-aminocyclohexyl)methane (PACM 20) or 1,8-diamino-4-(aminomethyl)octane (triaminononane) is the amine.

\* \* \* \* \*